(12) United States Patent
Shimizu et al.

(10) Patent No.: US 7,812,506 B2
(45) Date of Patent: Oct. 12, 2010

(54) PIEZOELECTRIC/ELECTROSTRICTIVE MEMBRANE TYPE MEASURING DEVICE

(75) Inventors: Hideki Shimizu, Ohbu (JP); Takao Ohnishi, Kiyosu (JP); Tomohiro Yamada, Komaki (JP)

(73) Assignee: NGK Insulators, Ltd., Nagoya (JP)

( * ) Notice: Subject to any disclaimer, the term of this patent is extended or adjusted under 35 U.S.C. 154(b) by 23 days.

(21) Appl. No.: 12/331,694

(22) Filed: Dec. 10, 2008

(65) Prior Publication Data

US 2009/0095072 A1 Apr. 16, 2009

Related U.S. Application Data

(63) Continuation of application No. PCT/JP2007/063374, filed on Jul. 4, 2007.

(30) Foreign Application Priority Data

| Jul. 4, 2006 | (JP) | ............................. 2006-184061 |
| Aug. 14, 2006 | (JP) | ............................. 2006-221129 |
| Mar. 14, 2007 | (JP) | ............................. 2007-065922 |

(51) Int. Cl.
   *H01L 41/08* (2006.01)
(52) U.S. Cl. .................... 310/324; 310/323.21
(58) Field of Classification Search ................ 310/324, 310/323.21
   See application file for complete search history.

(56) References Cited

U.S. PATENT DOCUMENTS

| 5,281,888 A | 1/1994 | Takeuchi et al. |
| 5,376,857 A | 12/1994 | Takeuchi et al. |
| 5,825,119 A * | 10/1998 | Shibata et al. .............. 310/338 |
| 5,889,351 A * | 3/1999 | Okumura et al. ............ 310/321 |
| 5,993,624 A | 11/1999 | Matsubara et al. |
| 6,360,606 B2 * | 3/2002 | Hirota et al. .................. 73/579 |
| 6,402,304 B1 * | 6/2002 | Qiu et al. ...................... 347/68 |
| 6,774,541 B1 * | 8/2004 | Fukui .......................... 310/358 |
| 2007/0220724 A1 * | 9/2007 | Ohnishi et al. ............. 29/25.35 |
| 2008/0072408 A1 * | 3/2008 | Sano et al. ................. 29/25.35 |

FOREIGN PATENT DOCUMENTS

| JP | 02-056902 A1 | 2/1990 |
| JP | 05-267742 A1 | 10/1993 |
| JP | 06-027071 A1 | 2/1994 |
| JP | 06-260694 A1 | 9/1994 |
| JP | 08-201265 A1 | 8/1996 |
| JP | 09-264863 A1 | 10/1997 |
| JP | 10-227655 A1 | 8/1998 |
| JP | 2005-164495 A1 | 6/2005 |

\* cited by examiner

*Primary Examiner*—J. SanMartin
(74) *Attorney, Agent, or Firm*—Burr & Brown (57) ABSTRACT

A piezoelectric/electrostrictive membrane type sensor is provided with a ceramic base body and a piezoelectric/electrostrictive element. The ceramic base body includes a thin diaphragm portion, a thick portion and a cavity formed by the portions. The piezoelectric/electrostrictive element is arranged on the ceramic base body and also includes a piezoelectric/electrostrictive body, and an upper electrode and a lower electrode sandwiching the piezoelectric/electrostrictive body. Further, the piezoelectric/electrostrictive body contains an alkaline metal or an alkaline earth metal, with the upper electrode and the lower electrode containing gold or platinum. When there is a change in the atmosphere at a place where the sensor is used, the sensor copes with such change and at least prevents the continuation of a low-quality measurement.

3 Claims, 3 Drawing Sheets

PIEZOELECTRIC/ELECTROSTRICTIVE MEMBRANE TYPE MEASURING DEVICE

TECHNICAL FIELD OF THE INVENTION

The present invention relates to a piezoelectric/electrostrictive membrane type measuring sensor capable of confirming the measurement reliability of the sensor itself.

BACKGROUND OF THE INVENTION

A piezoelectric/electrostrictive membrane type sensor can be used for measuring fluid characteristics such as viscosity, density and concentration by use of the electromechanical converting function of a piezoelectric/electrostrictive element in which a membrane-like piezoelectric/electrostrictive body disposed in the sensor is sandwiched between a pair of electrodes. For example, when the piezoelectric/electrostrictive membrane type sensor (the piezoelectric/electrostrictive element) is vibrated in a fluid, a mechanical resistance is received by the viscosity resistance of the fluid, and the electric constant of the piezoelectric/electrostrictive element changes in a constant relationship with respect to the mechanical resistance. Therefore, the sensor can detect these changes in constant relationship to measure the viscosity of the fluid. It is to be noted that any prior document having the same theme as or a theme in common with the following theme of the present invention does not seem to be present, but examples of a prior document for reference of the piezoelectric/electrostrictive membrane type sensor include Patent Documents 1 to 4.

Patent Document 1: JP-A-8-201265
Patent Document 2: JP-A-5-267742
Patent Document 3: JP-A-6-260694
Patent Document 4: JP-A-2005-164495

SUMMARY OF THE INVENTION

In recent years, the application of the above piezoelectric/electrostrictive membrane type sensor (also referred to simply as the sensor) has broadened. Therefore, the sensor is not necessarily used in a place suitable for the sensor of an electric system, and the sensor is frequently used in a rather harsh place. For example, in an application in which the properties of the electrolytic solution (diluted sulfuric acid) of a lead cell or the viscosity of the oil of an automobile is measured, owing to a measurement target (a fluid), a gas containing an oxide such as sulfur oxide ($SO_x$) or nitrogen oxide ($NO_x$) might volatilize to locally fill the periphery of a piezoelectric/electrostrictive body. In this case, insulating properties between electrodes might lower. Thus, a predetermined voltage is not applied to the piezoelectric/electrostrictive body, and eventually an output lowers to deteriorate the measurement precision.

Moreover, even in a case where there is only little possibility of the gasification of the measurement target (the fluid), when the sensor is used in, for example, a factory, a surrounding environment is sometimes an atmosphere having high temperature, high humidity and high corrosive gas concentration, depending on the factory. Even in this case, when the atmosphere extends around the sensor, the measurement precision of the piezoelectric/electrostrictive membrane type sensor might similarly be deteriorated to lower the reliability of a measured value.

To solve this problem, there can be considered means for covering the piezoelectric/electrostrictive membrane type sensor with, for example, a protective membrane made of a polymer resin to protect the sensor from the atmosphere (the environment). However, when the sensor is subjected to such a treatment, the piezoelectric/electrostrictive membrane type sensor (the piezoelectric/electrostrictive element) hardly vibrates due to the protective membrane, and the sensitivity of the sensor lowers, which then cannot perform a preferable countermeasure.

However, the measurement target (the fluid) and use environment of the piezoelectric/electrostrictive membrane type sensor have been familiarized. Therefore, consideration is usually given to the installation of the sensor so that these problems do not occur, and hence the cost increase due to the covering with the above protective membrane or lack of reliability due to the sensitivity lowering might be caused.

The present invention has been developed in view of such a situation, and an object thereof is to provide a piezoelectric/electrostrictive membrane type sensor which does not require a membrane attaching treatment such as the covering with the protective membrane; and even if the change in the operation atmosphere happens, it can cope with such a change and at least prevents the continuation of measurement with a lower reliability. As a result of investigations, it has been found that the above object can be achieved by the piezoelectric/electrostrictive membrane type sensor having a function capable of confirming the state of the sensor itself in addition to an original function of measuring fluid characteristics.

That is, first, according to the present invention, there is provided a piezoelectric/electrostrictive membrane type sensor which is configured to confirm the measurement reliability of the sensor itself, comprising: a ceramic base body having a thin diaphragm portion, a thick portion integrally provided on the peripheral edge of the thin diaphragm portion, and a cavity formed by the thin diaphragm portion and the thick portion so as to communicate with the outside; and a piezoelectric/electrostrictive element having a laminate structure arranged on the outer surface of the thin diaphragm portion of the ceramic base body and including a membrane-like piezoelectric/electrostrictive body and a pair of membrane-like electrodes between which the piezoelectric/electrostrictive element is sandwiched, the thin diaphragm portion of the ceramic base body being configured to vibrate in synchronization with the driving of the piezoelectric/electrostrictive element, wherein the piezoelectric/electrostrictive body contains an alkaline metal or an alkaline earth metal, and the electrodes contain gold or platinum.

Preferable examples of the alkaline metal or the alkaline earth metal include sodium.

Next, according to the present invention, there is provided a fluid characteristic measurement device comprising: the above piezoelectric/electrostrictive membrane type sensor; a power source which applies a voltage to drive the piezoelectric/electrostrictive element of the piezoelectric/electrostrictive membrane type sensor; electric constant monitor means for detecting the change of an electric constant accompanying the vibration of the thin diaphragm portion of the piezoelectric/electrostrictive membrane type sensor; and insulation resistance measurement means for measuring the insulation resistance of the pair of electrodes sandwiched between the piezoelectric/electrostrictive body of the piezoelectric/electrostrictive membrane type sensor.

In the fluid characteristic measurement device according to the present invention, in a case where the measurement of the insulation resistance between the pair of electrodes sandwiched between the piezoelectric/electrostrictive body is performed in a highly humid environment, the state of the sensor can be more clearly grasped.

The voltage which drives the piezoelectric/electrostrictive element is applied across the pair of electrodes, and an electric field is applied to the piezoelectric/electrostrictive body sandwiched between the electrodes. Examples of the electric constant include loss factor, phase, resistance, reactance, conductance, susceptance, inductance and capacitance. In particular, the loss factor or the phase having one maximum or minimum change point in the vicinity of the resonance frequency of the piezoelectric/electrostrictive body, is preferably used.

Furthermore, according to the present invention, there is provided a regeneration method of a piezoelectric/electrostrictive membrane type sensor in which the piezoelectric/electrostrictive membrane type sensor is used, and regenerated in a case where the insulation properties across a pair of electrodes between the piezoelectric/electrostrictive body of the piezoelectric/electrostrictive membrane type sensor lower due to the use of the sensor, the method comprising: a step of heating at least the piezoelectric/electrostrictive body of the piezoelectric/electrostrictive membrane type sensor (the piezoelectric/electrostrictive body heating step); a step of cleaning at least the piezoelectric/electrostrictive element by use of an acidic solution or pure water (the piezoelectric/electrostrictive element cleaning step); and a step of polarizing the piezoelectric/electrostrictive body (the piezoelectric/electrostrictive body polarizing step).

This regeneration method is the restoration of the insulation properties of the piezoelectric/electrostrictive membrane type sensor in which the insulation properties between the electrodes have been lowered. Due to this regeneration, a predetermined voltage is applied to the piezoelectric/electrostrictive body sandwiched between the electrodes.

Examples of the acidic solution for use in a manufacturing method and the regeneration method of the above piezoelectric/electrostrictive membrane type sensor include, for example diluted sulfuric acid and diluted hydrochloric acid, and the pure water having a specific resistance of 0.5 to 18 MΩ·cm (25° C.) is preferably used. The pure water is more preferable than the acidic solution in that the type of the electrode can be selected from a broad range (no corrosion caused).

In the piezoelectric/electrostrictive membrane type sensor according to the present invention, an oxide which is present in an environment where the sensor is used reacts with the alkaline metal or the alkaline earth metal contained in the piezoelectric/electrostrictive body on the surface of the piezoelectric/electrostrictive body, the oxide is adsorbed by the surface, and gold or platinum contained in the electrodes promotes the reaction as a catalyst. Consequently, the change of the insulation resistance between the electrodes appears, and the use environment (atmosphere) of the sensor, or the insulated state, that is, the measurement reliability of the sensor itself can be confirmed.

Moreover, the piezoelectric/electrostrictive body constituting the piezoelectric/electrostrictive membrane type sensor according to the present invention contains the alkaline metal or the alkaline earth metal, and the electrodes contain gold or platinum. Therefore, the oxide present in the environment where the sensor is used is easily adsorbed, a large amount of the oxide can be adsorbed owing to a small change, and the sensor has a high sensitivity.

In a case where the piezoelectric/electrostrictive membrane type sensor is constituted of, for example, the piezoelectric/electrostrictive body containing sodium, when sulfur oxide ($SO_X$) increases in a surrounding environment, sulfur oxide ($SO_X$) reacts with sodium contained in the piezoelectric/electrostrictive body, and is adsorbed by the surface of the piezoelectric/electrostrictive body, and a sodium-sulfur compound (e.g., sodium sulfate) is generated in the surface of the piezoelectric/electrostrictive body. Moreover, eventually a slight amount of short-circuit current easily flows across the electrodes, and the insulation resistance between the electrodes lowers. Therefore, when the insulation resistance between the electrodes is measured (e.g., after each predetermined time), the concentration of an oxide such as sulfur oxide ($SO_X$) present in the environment can be measured, and the change of the environment can sensitively be detected. The piezoelectric/electrostrictive membrane type sensor according to the present invention can be used as a sensor for measuring the concentration of the oxide present in such an environment or detecting the change of the environment.

In the piezoelectric/electrostrictive membrane type sensor constituted of a piezoelectric/electrostrictive body which does not contain the alkaline metal or the alkaline earth metal and electrodes which do not contain gold or platinum, any substance that easily reacts with a surrounding oxide such as sulfur oxide ($SO_X$) is not present in the piezoelectric/electrostrictive body, and any catalyst that promotes the reaction is not present, so that a surrounding oxide such as sulfur oxide ($SO_X$) is not easily adsorbed by the surface of the piezoelectric/electrostrictive body, and there is only little resistance change. In consequence, even when the change of the use environment occurs and the concentration of the oxide in the air increases, the presence of the oxide cannot be detected by the piezoelectric/electrostrictive membrane type sensor itself, and it is difficult to detect the change of the use environment (the atmosphere). Therefore, it is difficult to secure the measurement reliability of the sensor itself.

However, the piezoelectric/electrostrictive membrane type sensor according to the present invention can measure the concentration of the oxide present in the environment, detect the change of the environment and confirm the measurement reliability of the sensor itself. Therefore, in a case where the environment worsens, it proves clear that the measurement reliability lowers. In consequence, processing such as the correction of the measured value of the sensor itself can be performed, so that a sensing precision can be improved.

The piezoelectric/electrostrictive membrane type sensor according to the present invention includes the piezoelectric/electrostrictive element arranged on the thin diaphragm portion, and the thin diaphragm portion vibrates in synchronization with the driving of the piezoelectric/electrostrictive element, so that the sensor can be used as a heretofore known sensor for measuring fluid characteristics such as viscosity, density and concentration. For example, when the piezoelectric/electrostrictive membrane type sensor (the piezoelectric/electrostrictive element) is vibrated in the fluid, a mechanical resistance is received owing to the viscosity resistance of the fluid, and the electric constant of the piezoelectric/electrostrictive element changes in a definite relation with respect to the mechanical resistance, so that the electric constant can be detected to measure the viscosity of the fluid.

Therefore, it can be said that the piezoelectric/electrostrictive membrane type sensor according to the present invention is a fluid characteristic measuring sensor having an environment measuring function or an environment change detecting function. Moreover, a predetermined performance cannot necessarily be exerted during installation, depending on the environment. Consequently, it can be said that the sensor is a fluid characteristic measuring sensor having a self diagnosis function of diagnosing whether or not the sensor itself is installed in an environment where the performance can sufficiently be exerted, and being capable of correcting the measured value to restore the sensor itself.

According to a configuration of the fluid characteristic measurement device preferably of the present invention in which the piezoelectric/electrostrictive membrane type sensor of the present invention is used, when, for example, the viscosity of the fluid is measured, the concentration of sulfur oxide ($SO_X$) can be detected simultaneously with the measurement of the fluid viscosity to record both of them. Alternatively, at least the generation of the change of the environment can be detected to issue an alarm and correct the measured value. Therefore, in a case where the measurement target (the fluid) leaks or a factory situation changes unexpectedly to fill a place with a gas containing sulfur oxide ($SO_X$) where the piezoelectric/electrostrictive membrane type sensor is installed, a problem that the abnormality of the measured value due to the change of the environment is not noticed does not occur.

The fluid characteristic measurement device according to the present invention includes the above piezoelectric/electrostrictive membrane type sensor according to the present invention, the power source, the electric constant monitor means and the insulation resistance measurement means. This corresponds to one example of a specific configuration of a device which measures the characteristics of the fluid and measures the environment by use of the piezoelectric/electrostrictive membrane type sensor according to the present invention. According to the fluid characteristic measurement device of the present invention, the electric constant is detected by the electric constant monitor means, and the characteristics (e.g., the viscosity) of the fluid are measured. Moreover, the insulation resistance measurement means measures the insulation resistance between the electrodes, and measures the concentration of an oxide such as sulfur oxide ($SO_X$) present in the environment. In consequence, the excellent effect of the piezoelectric/electrostrictive membrane type sensor according to the present invention is derived.

When the piezoelectric/electrostrictive membrane type sensor according to the present invention is used in the highly humid atmosphere where the oxide is present, the oxide (e.g., sulfur oxide ($SO_X$)), or the compound (e.g., sodium sulfate) of the oxide with the alkaline metal or the alkaline earth metal (e.g., sodium) is deposited on the surface of the piezoelectric/electrostrictive element, and insulation properties between the electrodes lower. Consequently, even when an output on a power source side is constant, a predetermined voltage is not applied to the piezoelectric/electrostrictive body sandwiched between the electrodes. In this case, a normal measured value cannot be obtained by at least the fluid characteristic measuring sensor. Such piezoelectric/electrostrictive membrane type sensor according to the present invention that cannot be used any more and that has finished utility can be subjected to the regeneration method of the piezoelectric/electrostrictive membrane type sensor according to the present invention, and a usable state can be returned.

That is, according to the regeneration method of the piezoelectric/electrostrictive membrane type sensor according to the present invention, since the piezoelectric/electrostrictive element (the piezoelectric/electrostrictive body) is washed using the acidic solution or the pure water, the oxide (e.g., sulfur oxide ($SO_X$)) that has adhered to the surface of the piezoelectric/electrostrictive element, or the compound (e.g., sodium sulfate) generated by the reaction of the oxide with the alkaline metal or the alkaline earth metal (e.g., sodium) is removed, so that the insulation properties between the electrodes are restored and the predetermined voltage is applied to the piezoelectric/electrostrictive body sandwiched between the electrodes. Moreover, according to the regeneration method of the piezoelectric/electrostrictive membrane type sensor of the present invention, since the piezoelectric/electrostrictive element is polarized, the piezoelectric/electrostrictive body depolarized by heating and drying can be restored to a predetermined polarized state, and predetermined vibration can be obtained. Therefore, the used piezoelectric/electrostrictive membrane type sensor subjected to the regeneration method of the piezoelectric/electrostrictive membrane type sensor according to the present invention can normally work as the fluid characteristic measuring sensor.

Additionally, in the piezoelectric/electrostrictive membrane type sensor according to the present invention, when the oxide (e.g., sulfur oxide ($SO_X$)), or the compound (e.g., sodium sulfate) of the oxide with the alkaline metal or the alkaline earth metal (e.g., sodium) is deposited on the surface of the piezoelectric/electrostrictive element, a problem might occur that the precision in the measurement of the concentration of the oxide lowers or that sensitivity for detecting the change ratio of the concentration of the oxide dulls. However, when the oxide or the compound is eliminated by the regeneration method of the piezoelectric/electrostrictive membrane type sensor according to the present invention, the above problem can be solved. The environment is newly precisely measured, or the environment change detecting function can be exerted with a good sensitivity.

DESCRIPTION OF REFERENCE NUMERALS

1 ceramic base body
2 thick portion
3 thin diaphragm portion
4 lower electrode
5 piezoelectric/electrostrictive body
6 upper electrode
7B incompletely bonded portion
8 auxiliary electrode
9 through hole
10 cavity
11 (piezoelectric/electrostrictive body) flared portion
12 piezoelectric/electrostrictive element
20 piezoelectric/electrostrictive membrane type sensor
21 power source
22 electric constant monitor means
23 insulation resistance measurement means
40 fluid characteristic measurement device

DETAILED DESCRIPTION OF THE INVENTION

Embodiments of the present invention will hereinafter be described appropriately with reference to the drawings, but the present invention is not limited to these embodiments when interpreted. The present invention can variously be changed, modified, improved and replaced based on the knowledge of any person skilled in the art without departing from the scope of the present invention. For example, the drawings show the preferable embodiments of the present invention, but the present invention is not restricted by configuration or information shown in the drawings. To implement or verify the present invention, means similar or equivalent to means described in the present description is applicable, but preferable means is the following means.

Figure 1:
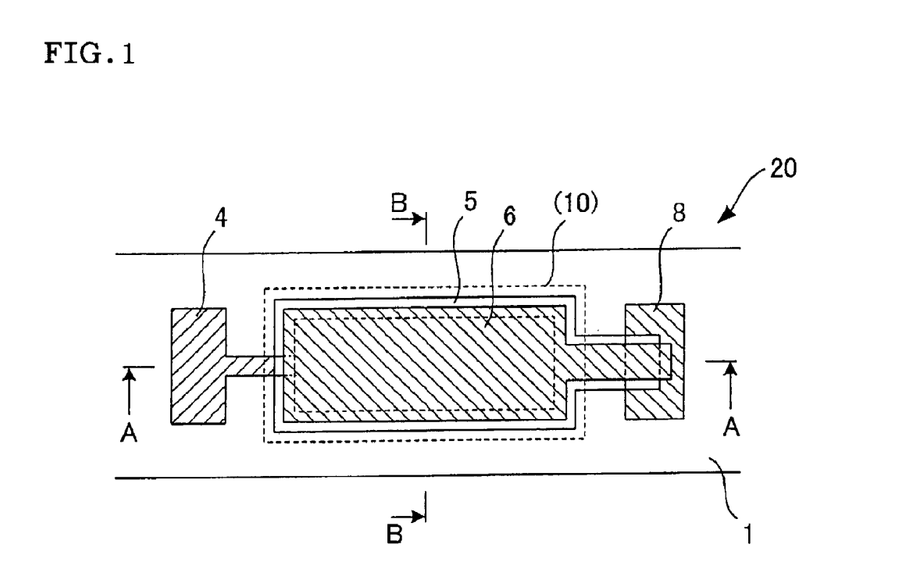
FIG. 1 is a plan view showing one embodiment of a piezoelectric/electrostrictive membrane type sensor according to the present invention.
Figure 2:
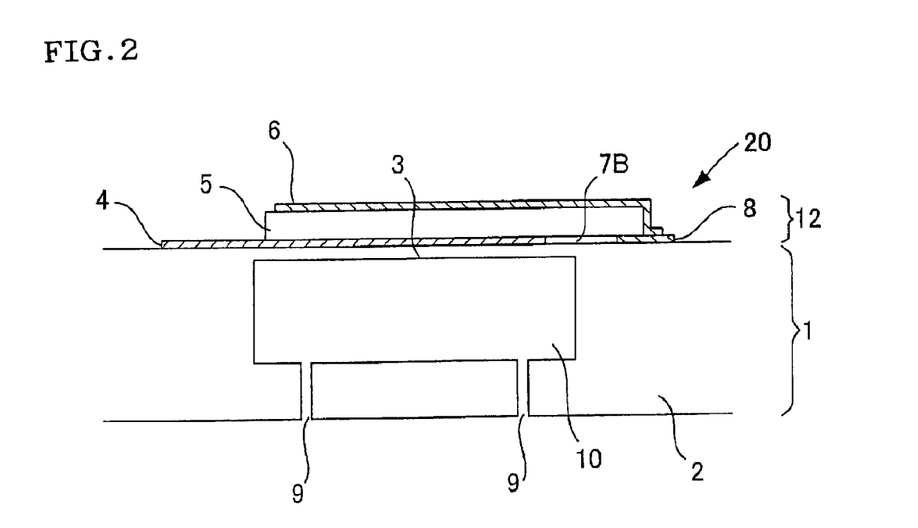
FIG. 2 is a sectional view showing a section cut along the line AA in FIG. 1.
Figure 3:
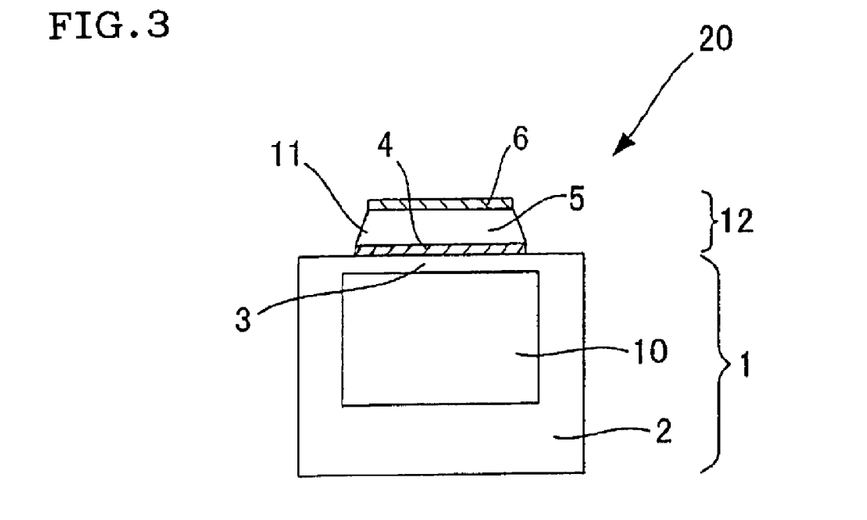
FIG. 3 is a sectional view showing a section cut along the line BB in FIG. 1.

First, the constitution of a piezoelectric/electrostrictive membrane type sensor according to the present invention will be described. FIG. 1 is a plan view (a top view) showing one embodiment of the piezoelectric/electrostrictive membrane type sensor according to the present invention, FIG. 2 is a sectional view showing a section cut along the line AA in FIG. 1, and FIG. 3 is a sectional view showing a section cut along the line BB in FIG. 1. A piezoelectric/electrostrictive membrane type sensor 20 shown in FIGS. 1 to 3 includes a ceramic base body 1 and a piezoelectric/electrostrictive element 12. The ceramic base body 1 has a thin diaphragm portion 3 and a thick portion 2 integrally provided on the peripheral edge of the thin diaphragm portion 3, and the ceramic base body 1 is provided with a cavity 10 formed by the thin diaphragm portion 3 and the thick portion 2 so as to communicate with the outside via through holes 9. The piezoelectric/electrostrictive element 12 is arranged on the outer surface of the thin diaphragm portion 3 of the ceramic base body 1, and has a laminate structure formed by a membrane-like piezoelectric/electrostrictive body 5 and a pair of membrane-like electrodes (an upper electrode 6 and a lower electrode 4) sandwiching the piezoelectric/electrostrictive body 5 therebetween.

In the piezoelectric/electrostrictive membrane type sensor 20, the lower electrode 4 is formed with a length extending to a position where one end of the lower electrode on the side of an auxiliary electrode 8 does not extend beyond the thin diaphragm portion 3. The auxiliary electrode 8 is formed so that an incompletely bonded portion 7B is sandwiched and so that the auxiliary electrode enters the downside of the piezoelectric/electrostrictive body 5 independently of the lower electrode 4. One end of the lower electrode 4 and the auxiliary electrode 8 disposed on the thick portion 2 can serve as lead terminals. A layer form binding the piezoelectric/electrostrictive body 5 and the thin diaphragm portion 3 may be formed at the incomplete bonding portion (between the lower electrode 4 and the auxiliary electrode 8). The piezoelectric/electrostrictive body 5 is formed in such a size as to straddle the lower electrode 4 and the auxiliary electrode 8 and cover the lower electrode 4. The upper electrode 6 is formed so as to straddle the piezoelectric/electrostrictive body 5 and the auxiliary electrode 8 and conduct electricity to the auxiliary electrode 8. The piezoelectric/electrostrictive body 5 is provided with a flared portion 11. However, when the decrease of electric constant fluctuation or change over time is demanded as sensor characteristics, the size of the lower electrode 4 is set to a size substantially equal to that of the piezoelectric/electrostrictive body 5, and the flared portion 11 may be eliminated.

In the piezoelectric/electrostrictive membrane type sensor 20, when the piezoelectric/electrostrictive element 12 is driven (displacement is generated), the thin diaphragm portion 3 of the ceramic base body 1 vibrates in synchronization with the driving. The thin diaphragm portion 3 of the ceramic base body 1 usually has a thickness of 50 μm or less, preferably 30 μm or less, further preferably 15 μm or less so that the vibration of the piezoelectric/electrostrictive body 5 is not disturbed. As the planar shape of the thin diaphragm portion 3, any shape such as a rectangular shape, a square shape, a triangular shape, an elliptic shape or a perfectly circular shape may be employed, but the rectangular shape or the perfectly circular shape is selected if necessary, in the application of the sensor in which a resonance mode to be excited needs to be simplified.

Next, the material of each constitutional requirement of the piezoelectric/electrostrictive membrane type sensor according to the present invention will be described in accordance with the piezoelectric/electrostrictive membrane type sensor 20 as an example. The material for use in the ceramic base body 1 is preferably a material having thermal resistance, chemical stability and insulation properties. This is because the lower electrode 4, the piezoelectric/electrostrictive body 5 and the upper electrode 6 are sometimes thermally treated when integrated into one unit, and a solution sometimes has conductivity or corrosive properties when the piezoelectric/electrostrictive membrane type sensor senses the characteristics of the solution. Examples of a preferably usable material include stabilized zirconium oxide, aluminum oxide, magnesium oxide, mullite, aluminum nitride, silicon nitride and glass. Among these materials, stabilized zirconium oxide is most preferable because the material keeps a high mechanical strength or has an excellent tenacity or the like even in a case where the thin diaphragm portion is formed remarkably thin.

As the material of the piezoelectric/electrostrictive body 5, any material may be used as long as the material contains an alkaline metal or an alkaline earth metal, and exerts a piezoelectric/electrostrictive effect. Examples of a preferable material satisfying the conditions include $(Bi_{0.5}Na_{0.5})TiO_3$ or a material containing this component as a main component, or $(1-x)(Bi_{0.5}Na_{0.5})TiO_3-xKNbO_3$ (x is a molar fraction of $0 \leq x \leq 0.06$) or a material containing this component as the main component.

To provide a bonding layer, as the material of the layer, an organic or inorganic material having close contact properties and bonding properties with respect to both the piezoelectric/electrostrictive body 5 and the ceramic base body 1 may be used. The material for use preferably has a thermal expansion coefficient having an intermediate value between the thermal expansion coefficient of the material of the ceramic base body 1 and the thermal expansion coefficient of the material for use in the piezoelectric/electrostrictive body 5 in order to obtain highly reliable bonding properties. When the piezoelectric/electrostrictive body 5 is thermally treated, a glass material having a softening point higher than the thermal treatment temperature of the piezoelectric/electrostrictive body 5 is preferably used. The piezoelectric/electrostrictive body 5 is firmly bonded to the ceramic base body 1, and deformation by the thermal treatment is suppressed owing to the high softening point. Furthermore, when the piezoelectric/electrostrictive body 5 is constituted of the above material, as the material of the bonding layer, a material containing $(1-x)(Bi_{0.5}Na_{0.5})TiO_3-xKNbO_3$ (x is a molar fraction of $0.08 \times 0.5$) as the main component is preferably employed. This is because the material has high close contact properties with respect to both the piezoelectric/electrostrictive body 5 and the ceramic base body 1, and the piezoelectric/electrostrictive body 5 and the ceramic base body 1 can be prevented from being adversely affected during the thermal treatment. That is, since the material has a component similar to that of the piezoelectric/electrostrictive body 5, the material has high close contact properties with respect to the piezoelectric/electrostrictive body 5. Moreover, there are fewer problems due to the diffusion of a heterologous element which might be generated in a case where glass is used. Furthermore, since much KNbO$_3$ is contained, the material has a high reactivity with the ceramic base body 1, and firm bonding is possible. In addition, (1-x)(Bi$_{0.5}$Na$_{0.5}$)TiO$_3$-xKNbO$_3$ (x is the molar fraction of 0.08× 0.5) hardly exerts piezoelectric/electrostrictive characteristics. Therefore, during use, any displacement is not generated with respect to an electric field generated in the lower electrode 4 and the auxiliary electrode 8, and hence stable sensor characteristics can be obtained.

As to the material of the electrodes (the upper electrode 6, the lower electrode 4 and the auxiliary electrode 8), gold or an alloy containing gold as the main component, or platinum or an alloy containing platinum as the main component is used. It is to be noted that rhodium is added as the material of the upper electrode 6 to improve the thermal resistance of the electrode, so that firing contraction can be controlled, and both covering properties and denseness can be achieved at the same time. Moreover, when (1-x)(Bi$_{0.5}$Na$_{0.5}$)TiO$_3$-xKNbO$_3$ is combined, a Schottky barrier wall of an interface between the electrode and a ceramic material varies owing to the amount of rhodium to be added, and hence initial insulation resistance can be controlled.

Next, a manufacturing method of the piezoelectric/electrostrictive membrane type sensor according to the present invention will be described in accordance with the manufacturing of the above piezoelectric/electrostrictive membrane type sensor 20 as an example. The ceramic base body 1 can be prepared by a green sheet laminating process. Specifically, the predetermined number of ceramic green sheets constituted of the above-mentioned ceramic material as the main component are prepared. A hole portion having a predetermined shape constituting the cavity 10 after the lamination is made in the necessary number of the resultant ceramic green sheets by use of a punch processor including, for example, a punch and a die, and hole portions having a predetermined shape forming the through holes 9 are made in the necessary number of the laminated sheets. Then, the ceramic green sheet constituting the thin diaphragm portion 3, the ceramic green sheet having the hole portion made so as to constitute the cavity 10, and the ceramic green sheet having the hole portion made so as to constitute the through holes 9 are laminated in this order, to obtain a laminated green body, and the body is fired to obtain the ceramic base body 1.

It is to be noted that the ceramic green sheet can be prepared by a heretofore known ceramic manufacturing method. For example, ceramic material powder is prepared, and blended, so as to obtain a desired composition, with a binder, a solvent, a dispersant, a plasticizer or the like to prepare a slurry, and this slurry is subjected to a defoaming treatment and then the ceramic green sheet can be obtained through a sheet forming process such as a doctor blade process, a reverse roll coater process or a reverse doctor roll coater process.

After separately preparing the piezoelectric/electrostrictive element 12 only, the element may be attached to the ceramic base body 1, or may directly be formed on the ceramic base body 1. In the latter case, the element is prepared, for example, as follows. First, the lower electrode 4 and the auxiliary electrode 8 are formed on the outer surface of the thin diaphragm portion 3 of the ceramic base body 1 by any type of known membrane forming technique. Specifically, a thin membrane forming technique such as ion beam, sputtering, vacuum deposition, CVD, ion plating or plating or a thick membrane forming technique such as screen printing, spray or dipping is appropriately selected. In particular, the sputtering process and the screen printing process is preferably selected.

To provide the bonding layer, a usual thick membrane technique is used in the formation. In particular, a stamping process or the screen printing process is used. Moreover, when a portion to be formed has a size of about several ten μm to several hundred μm, an ink jet process is preferably used. When the bonding layer needs to be thermally treated, the layer may thermally be treated before forming the next piezoelectric/electrostrictive body 5, or may thermally be treated simultaneously with the piezoelectric/electrostrictive body 5 after forming the body.

The piezoelectric/electrostrictive body 5 is formed by any known membrane forming process in the same manner as in the lower electrode 4 and the auxiliary electrode 8. From a viewpoint of cost reduction, the screen printing is preferably used. The thus formed piezoelectric/electrostrictive body 5 is thermally treated, if necessary, and the body is integrated with the lower electrode 4, the auxiliary electrode 8 and the bonding layer. A thermal treatment temperature is in a range of about 900° C. to 1400° C. At the time of thermal treatment, it is preferable to control the atmosphere together with an evaporation source of the piezoelectric/electrostrictive material so as not to make the piezoelectric/electrostrictive body 5 unstable at a high temperature.

The upper electrode 6 is formed by a membrane forming process similar to that of the lower electrode 4 and the auxiliary electrode 8. Moreover, after forming a membrane, the upper electrode 6 is thermally treated if necessary, and bonded to the piezoelectric/electrostrictive body 5 and the auxiliary electrode 8 to form an integral structure.

It is to be noted that to bond the lower electrode 4, the bonding layer, the piezoelectric/electrostrictive body 5 and the upper electrode 6 by the thermal treatment, the membrane may thermally be treated every time each membrane is formed. Alternatively, the membranes may successively be formed, and then simultaneously thermally treated. During the thermal treatment, to obtain satisfactory bonding properties and suppress alteration due to the diffusion of any constituent element, needless to say, the thermal treatment temperature is appropriately selected.

According to the above steps, the piezoelectric/electrostrictive membrane type sensor 20 including the ceramic base body 1 and the piezoelectric/electrostrictive element 12 is structurally completed. Next, the whole piezoelectric/electrostrictive membrane type sensor 20 (at least the piezoelectric/electrostrictive element 12) is washed off using an acidic solution or pure water. By this washing, an alkaline metal or an alkaline earth metal which is contained in the piezoelectric/electrostrictive body 5 and which is present on the surface of the body is removed. In a case where a material containing (Bi$_{0.5}$Na$_{0.5}$)TiO$_3$ as a main component is selected as the material of the piezoelectric/electrostrictive body 5, sodium which might be present on the surface of the piezoelectric/electrostrictive body 5 is removed. Since sodium as the alkaline metal is removed, the piezoelectric/electrostrictive membrane type sensor 20 as a product to be shipped keeps the insulation properties of the surface of the piezoelectric/electrostrictive body 5 even in a highly humid environment.

Furthermore, a direct-current high voltage is applied to the piezoelectric/electrostrictive body 5 to perform a polarization treatment. In the polarization treatment, a pulsed voltage is preferably applied so that the magnitude of the voltage increases in accordance with the increase of the number of application times. As compared with a case where the voltage is not applied in this manner, a polarization ratio can be increased in a short time. This is supposedly based on the polarization treatment performed while easing a stress interposed in the piezoelectric/electrostrictive body 5. Furthermore, after the polarization treatment, the piezoelectric/electrostrictive body is heated at a temperature of 80 to 100° C. Then, after the value of the electric constant of the piezoelectric/electrostrictive body 5 converges (at a time when the value converges), the piezoelectric/electrostrictive body 5 is further preferably subjected to the polarization treatment again. This is because the characteristics of the piezoelectric/electrostrictive membrane type sensor can be stabilized. It is to be noted that as the electric constant of the piezoelectric/electrostrictive body 5, capacitance, loss factor, resistance, reactance, conductance, susceptance, inductance or the like may appropriately be employed.

Next, a regeneration method of the piezoelectric/electrostrictive membrane type sensor according to the present invention will be described in accordance with the piezoelectric/electrostrictive membrane type sensor 20 as an example. The piezoelectric/electrostrictive membrane type sensor 20 is prepared by the above-mentioned manufacturing method, but this piezoelectric/electrostrictive membrane type sensor 20 has an environment measuring function or an environment change detecting function. Such a function is realized, when the piezoelectric/electrostrictive body 5 contains the alkaline metal or the alkaline earth metal, and the electrodes (the upper electrode 6, the lower electrode 4, etc.) contain gold or platinum and a surrounding oxide (e.g., sulfur oxide ($SO_x$)) is therefore adsorbed. Therefore, in a case where this piezoelectric/electrostrictive membrane type sensor 20 is incorporated in, for example, a fluid characteristic measurement device described later and is actually used in a site such as a factory, the oxide, a compound or the like is deposited on the surface of the piezoelectric/electrostrictive body 5, as long as a use environment is not a special place such as a clean room, although there is a difference of a degree of time, depending on the conditions of the environment. Therefore, insulation properties between the upper electrode 6 and the lower electrode 4 finally lower, and the sensor cannot be used any more as the fluid characteristic measuring sensor, and finishes its utility.

Therefore, in a case where the piezoelectric/electrostrictive membrane type sensor 20 has finished this utility, in other words, in a case where the insulation properties between the upper electrode 6 and the lower electrode 4 lower as much as a predetermined value or more as compared with a shipping time, the sensor is detached from, for example, the fluid characteristic measurement device, and brought back to a regeneration factory where the piezoelectric/electrostrictive membrane type sensor 20 is washed using the acidic solution or the pure water. By such cleaning, the oxide, the compound or the like adsorbed by or adhering to the surface of the piezoelectric/electrostrictive body 5 is removed. By this removal, the insulation properties of the surface of the piezoelectric/electrostrictive body 5 are kept even in the highly humid environment in the same manner as in the shipped product. In this case, needless to say, the insulation properties between the electrodes are also restored, and the piezoelectric/electrostrictive membrane type sensor 20 becomes reusable. Moreover, when the sensor is heated to dry, the piezoelectric/electrostrictive body 5 needs to be polarized again. Owing to this polarization, the piezoelectric/electrostrictive characteristics of the piezoelectric/electrostrictive element 12 can be the same as those of the shipped product.

Figure 4:
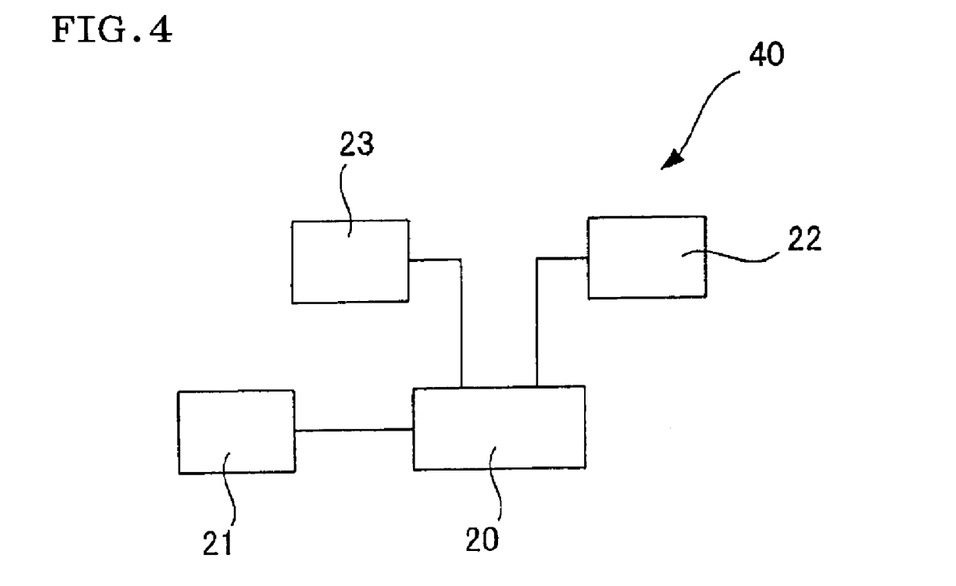
FIG. 4 is a constitution diagram showing one embodiment of a fluid characteristic measurement device according to the present invention.

Next, a fluid characteristic measurement device according to the present invention will be described. FIG. 4 is a constitution diagram showing one embodiment of the fluid characteristic measurement device according to the present invention. A fluid characteristic measurement device 40 shown in FIG. 4 includes the above-mentioned piezoelectric/electrostrictive membrane type sensor 20; a power source 21 which applies a voltage across the upper electrode 6 and lower electrode 4 so as to drive the piezoelectric/electrostrictive element 12 of the piezoelectric/electrostrictive membrane type sensor 20; electric constant monitor means 22 for detecting the change of an electric constant accompanying the vibration of the thin diaphragm portion 3 of the piezoelectric/electrostrictive membrane type sensor 20; and insulation resistance measurement means 23 for measuring the insulation resistance between the upper electrode 6 and the lower electrode 4 in the piezoelectric/electrostrictive membrane type sensor 20. The device further includes humidifying means (not shown).

The fluid characteristic measurement device 40 is a device including the electric constant monitor means 22 and capable of detecting the electric constant to measure the characteristics of the fluid. For example, when the piezoelectric/electrostrictive element 12 is driven in the piezoelectric/electrostrictive membrane type sensor 20 to vibrate the thin diaphragm portion 3 in the fluid, a mechanical resistance is received owing to the viscosity resistance of the fluid, and the electric constant of the piezoelectric/electrostrictive element 12 changes in a constant relation with respect to the mechanical resistance. Therefore, the change can be detected to measure the viscosity of the fluid. Moreover, since the fluid characteristic measurement device 40 includes the insulation resistance measurement means 23, the insulation resistance between the upper electrode 6 and the lower electrode 4 can be measured, for example, after each predetermined time, whereby the concentration of an oxide such as sulfur oxide ($SO_x$) present in the environment can be measured. Therefore, the fluid characteristic measurement device 40 is a device capable of measuring the environment while measuring the characteristics of the fluid. Furthermore, when the insulation resistance is measured, the piezoelectric/electrostrictive element 12 can be humidified by the humidifying means to confirm whether or not the state of the surface of the device itself can more precisely secure the reliability of the measurement.

In the basic principle of the fluid characteristic measurement device according to the present invention in measuring the characteristics of the fluid, there is used a correlation between the amplitudes of the piezoelectric/electrostrictive element and the thin diaphragm portion as vibrators and the characteristics of the fluid which comes in contact with the vibrators. In a case where the fluid has the characteristics of, for example, the viscosity resistance, when the fluid has a large viscosity resistance, the amplitudes of the vibrators decrease. When the viscosity resistance decreases, the amplitudes of the vibrators increase.

Moreover, a vibration configuration in a mechanical system, for example, the vibration of the vibrator can be replaced with an equivalent circuit of an electric system. In this case, it may be supposed that the amplitude corresponds to current. Moreover, the vibration state of the equivalent circuit indicates the changes of various electric constants in the vicinity of a resonance point. In the fluid characteristic measurement device according to the present invention, the loss factor or the phase having one maximum or minimum change point of the change in the vicinity of the resonance frequency of the equivalent circuit is preferably used as an index, among electric constants such as the loss factor, phase, resistance, reactance, conductance, susceptance, inductance and capacitance. The detection of the loss factor or the phase can more easily be performed as compared with the other electric constants.

Needless to say, even in a case where the fluid has characteristics other than the viscosity resistance, when an element influencing the vibration of the vibrator is present in the fluid having the characteristics to be measured, the characteristics may be associated with the changes of the vibrations of the piezoelectric/electrostrictive element and the thin diaphragm portion to measure the characteristics. When the fluid is, for example, a solution and the concentration of the solution changes to change viscosity or density, the vibration configurations of the piezoelectric/electrostrictive element and the thin diaphragm portion in the solution change, so that the concentration of the solution can be measured. That is, the fluid characteristic measurement device according to the present invention can measure the viscosity, density and concentration of the solution.

EXAMPLES

The present invention will hereinafter be described in more detail with respect to examples, but the present invention is not limited to these examples.

Six piezoelectric/electrostrictive membrane type sensors having the same configuration (without any bonding layer) as that of the above piezoelectric/electrostrictive membrane type sensor 20 were prepared. First, the powder of stabilized zirconium oxide, a binder and a dispersant were mixed to prepare a slurry, this slurry was subjected to a defoaming treatment, and the resultant material was formed by a doctor blade process to obtain a plurality of ceramic green sheets. Then, hole portions were made in the ceramic green sheets, if necessary. The ceramic green sheet constituting a thin diaphragm portion later, the ceramic green sheet in which the hole portion constituting a cavity was made, and the ceramic green sheet in which the hole portions constituting through holes were made were laminated in this order, and pressed to obtain a green laminate. Afterward, the green laminate was fired to obtain a ceramic base body.

Next, the resultant thin diaphragm portion of the ceramic base body was successively coated with a paste containing platinum as a main component, a paste of a piezoelectric/electrostrictive material containing $(Bi_{0.5}Na_{0.5})TiO_3$ as a main component, and a paste containing gold as a main component by a screen printing process, and the respective pastes were fired to form a piezoelectric/electrostrictive element constituted of a lower electrode, an auxiliary electrode, a piezoelectric/electrostrictive body and an upper electrode, thereby obtaining a non-washed non-polarized piezoelectric/electrostrictive membrane type sensor.

Then, the piezoelectric/electrostrictive membrane type sensor was washed using pure water having a specific resistance of 1 MΩ·cm, and then a direct-current voltage of 40 V was applied to perform a polarization treatment.

As described above, 6 piezoelectric/electrostrictive membrane type sensors A1, A2, A3, B1, B2 and B3 were prepared. When the initial insulation resistances of four sensors of them were measured, values were $8.05 \times 10^{10} \Omega$ (A1), $8.00 \times 10^{10} \Omega$ (A2), $8.00 \times 10^{10} \Omega$ (B1) and $8.10 \times 10^{10} \Omega$ (B2) respectively.

Moreover, the sensors A1, A2 and A3 were vacuum-packed, and stored in a room of a factory for one day (24 hours). On the other hand, the sensors B1, B2 and B3 were left to stand as they were in the factory room for one day (24 hours) without being vacuum-packed. The factory room had an initial humidity of 30%, and a temperature of 24° C. After the elapse of one day, the room had a humidity of 80% and a temperature of 24° C. When the insulation resistances of the four piezoelectric/electrostrictive membrane type sensors A1, A2, B1 and B2 of the six piezoelectric/electrostrictive membrane type sensors A1, A2, A3, B1, B2 and B3 stored or left to stand for one day were measured, the values were $1.50 \times 10^{10} \Omega$ (A1), $1.50 \times 10^{10} \Omega$ (A2), $8.00 \times 10^{8} \Omega$ (B1) and $8.10 \times 10^{8} \Omega$ (B2), respectively. The insulation resistance of the piezoelectric/electrostrictive membrane type sensor left to stand in the factory room largely lowered as compared with that of the vacuum-packed sensor.

Figure 5:
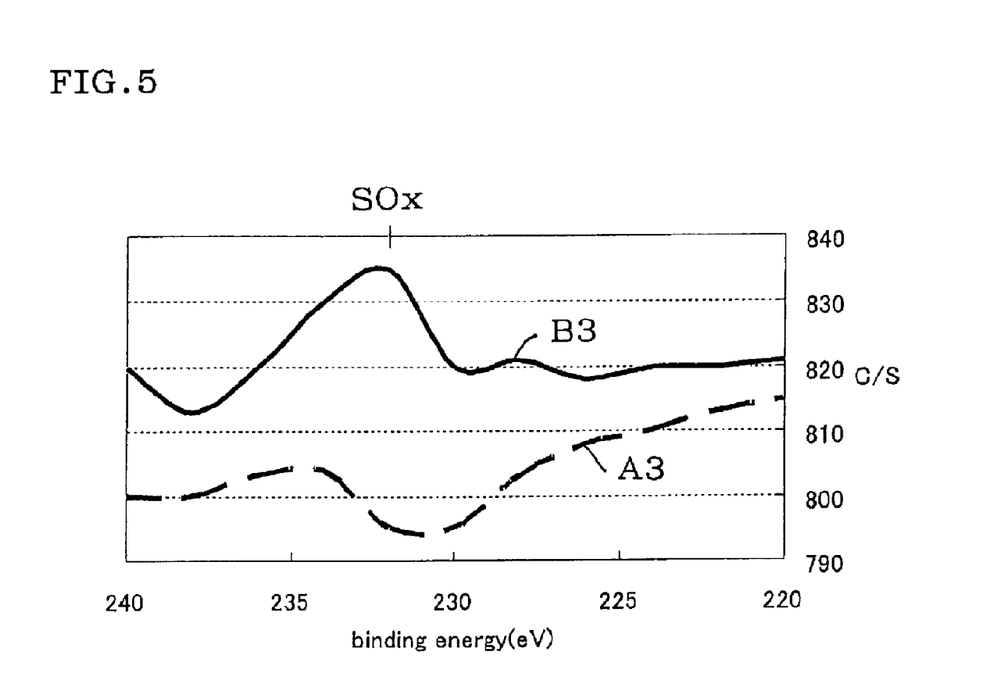
FIG. 5 is a chart showing the result of the measurement of the amount of sulfur oxide ($SO_X$) present on the surface of the piezoelectric/electrostrictive membrane type sensor in an example with X-ray photoelectron spectroscopy.

The 2 remaining sensors A3, B3 continued to be stored or left to stand, and stored or left to stand in the factory room for six days in total. Then, the surfaces of the 2 piezoelectric/electrostrictive membrane type sensor A3, B3 stored or left to stand for six days were analyzed using X-ray photoelectron spectroscopy. Results are shown in FIG. 5. In FIG. 5, the abscissa indicates binding energy, and the ordinate indicates strength per unit second. As shown in FIG. 5, on the surface of the piezoelectric/electrostrictive membrane type sensor (B3) left to stand in the factory room, the intensity of the binding energy corresponding to $SO_X$ around 232 eV increased as compared with the vacuum-packed sensor (A3). That is, a large amount of sulfur oxide ($SO_X$) adhered to the surface of the sensor.

INDUSTRIAL APPLICABILITY

A piezoelectric/electrostrictive membrane sensor according to the present invention can be used as a sensor for measuring the characteristics of a fluid and/or a sensor for measuring the concentration of an oxide (e.g., sulfur oxide ($SO_X$)) (in air). According to the piezoelectric/electrostrictive membrane type sensor of the present invention, while measuring an environment (or detecting the change of the environment), the characteristics of the fluid can be measured. Therefore, the piezoelectric/electrostrictive membrane type sensor according to the present invention can preferably be used as the sensor for measuring the characteristics of the fluid in a case where the fluid as a measurement target is an electrolytic solution (diluted sulfuric acid) of a lead cell, any type of oil or a battery solution, and the item of the fluid to be measured is a concentration or the like.

The invention claimed is:

1. A fluid characteristic measurement device comprising:
   a piezoelectric/electrostrictive membrane type sensor including
      a ceramic base body having a thin diaphragm portion, a thick portion integrally provided on the peripheral edge of the thin diaphragm portion, and a cavity formed by the thin diaphragm portion and the thick portion so as to communicate with the outside, and
      a piezoelectric/electrostrictive element having a laminate structure arranged on the outer surface of the thin diaphragm portion of the ceramic base body and including a membrane-like piezoelectric/electrostrictive body and a pair of membrane-like electrodes between which the piezoelectric/electrostrictive element is sandwiched, the thin diaphragm portion of the ceramic base body being configured to vibrate in synchronization with the driving of the piezoelectric/electrostrictive element,
      wherein the piezoelectric/electrostrictive body contains an alkaline metal or an alkaline earth metal, and the electrodes contain gold or platinum;
   a power source which applies a voltage to drive the piezoelectric/electrostrictive element of the piezoelectric/electrostrictive membrane type sensor;
   electric constant monitor means for detecting the change of an electric constant accompanying the vibration of the thin diaphragm portion of the piezoelectric/electrostrictive membrane type sensor; and insulation resistance measurement means for measuring the insulation resistance of the pair of electrodes between which the piezoelectric/electrostrictive body is sandwiched in the piezoelectric/electrostrictive membrane type sensor.

2. The fluid characteristic measurement device according to claim 1, wherein the measurement of the insulation resistance is performed in a highly humid environment.

3. A regeneration method for a piezoelectric/electrostrictive membrane type sensor, comprising:

providing a piezoelectric/electrostrictive membrane type sensor including a ceramic base body having a thin diaphragm portion, a thick portion integrally provided on the peripheral edge of the thin diaphragm portion, and a cavity formed by the thin diaphragm portion and the thick portion so as to communicate with the outside, and a piezoelectric/electrostrictive element having a laminate structure arranged on the outer surface of the thin diaphragm portion of the ceramic base body and including a membrane-like piezoelectric/electrostrictive body and a pair of membrane-like electrodes between which the piezoelectric/electrostrictive element is sandwiched, the thin diaphragm portion of the ceramic base body being configured to vibrate in synchronization with the driving of the piezoelectric/electrostrictive element, wherein the piezoelectric/electrostrictive body contains an alkaline metal or an alkaline earth metal, and the electrodes contain gold or platinum, regenerating the sensor in a case where the insulation properties across a pair of electrodes between which the piezoelectric/electrostrictive body is sandwiched in the piezoelectric/electrostrictive membrane type sensor becomes lower owing to the use of the sensor, the method including a step of heating at least the piezoelectric/electrostrictive body of the piezoelectric/electrostrictive membrane type sensor, a step of washing at least the piezoelectric/electrostrictive element by use of an acidic solution or pure water, and a step of polarizing the piezoelectric/electrostrictive body.

\* \* \* \* \*